United States Patent [19]

Tamai et al.

[11] Patent Number: 4,474,800
[45] Date of Patent: Oct. 2, 1984

[54] EPOXYSUCCINYL AMINO ACID DERIVATIVES

[75] Inventors: Masaharu Tamai; Shigeo Morimoto; Takashi Adachi; Kiyoshi Oguma; Kazunori Hanada; Sadafumi Omura, all of Saitama, Japan

[73] Assignee: Taisho Pharmaceutical Co., Ltd., Tokyo, Japan

[21] Appl. No.: 149,312

[22] Filed: May 13, 1980

[51] Int. Cl.³ .................. C07D 303/48; A61K 31/335
[52] U.S. Cl. ...................................... 424/278; 549/549
[58] Field of Search ................. 260/348.47; 424/278; 549/549

[56] References Cited

U.S. PATENT DOCUMENTS 3,911,111 10/1975 Sawada et al. .................... 424/118
4,064,241 12/1977 Ross et al. ......................... 424/246

FOREIGN PATENT DOCUMENTS 2809036 9/1978 Fed. Rep. of Germany .

OTHER PUBLICATIONS

K. Hanada et al., Agric. Biol. Chem., vol. 42(3), (1978), pp. 529–536; 537–541.
Chemical Abstracts, vol. 87: 68128z; 68129a; 85238c; 202108y; 202125b.

*Primary Examiner*—Norma S. Milestone
*Attorney, Agent, or Firm*—Wenderoth, Lind & Ponack

[57] ABSTRACT

An epoxysuccinyl amino acid derivative of the formula

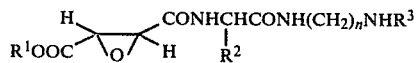

wherein $R^1$ is hydrogen, alkali metal, benzyl or cycloalkyl having 5 to 6 carbon atoms, $R^2$ is alkyl having 3 to 4 carbon atoms, $R^3$ is hydrogen, benzyloxycarbonyl, acetyl or benzoyl, and n is an integer of 2 to 7. The subject compounds exhibit inhibitory activity towards thiol protease, especially, calcium-activated neutral thiol protease which exists in excess in muscle tissues of mammals afflicted with muscular dystrophy.

3 Claims, No Drawings

EPOXYSUCCINYL AMINO ACID DERIVATIVES

BACKGROUND AND BRIEF SUMMARY OF THE INVENTION

The present invention relates to a novel epoxysuccinyl amino acid derivative of the formula

$$\underset{R^1OOC}{H}\!\!\diagdown\!\!\underset{O}{\diagup}\!\!\diagdown\!\!\underset{H}{\diagup}\!\!\overset{CONHCHCONH(CH_2)_nNHR^3}{\underset{R^2}{|}} \quad (I)$$

wherein $R^1$ is hydrogen, alkali metal, benzyl or cycloalkyl having 5 to 6 carbon atoms, $R^2$ is alkyl having 3 to 4 carbon atoms, $R^3$ is hydrogen, benzyloxycarbonyl, acetyl or benzoyl, and n is an integer of 2 to 7.

The prior art discloses E-64, ie., N-[N-(L-3-trans-carboxyoxirane-2-carbonyl)-L-leucyl]agmatine (U.S. Pat. No. 3,911,111), its intermediates [*Chemical Abstracts*, 87, 202108y (1977), ibid., 87, 85238c (1977), ibid., 87, 202125b (1977), ibid., 87, 68128z (1977)], and epoxysuccinic acid derivatives of German Patent Laid Open Application No. P 28 09 036 and *Chemical Abstracts*, 87, 681239a (1977) prepared by several of the present inventors.

The compounds of the present invention are distinguished from the prior art compounds by inhibitory activity to thiol protease, especially, calcium-activated neutral thiol protease (hereinafter referred to as CANP) which exists in excess in muscle tissues of mammals afflicted with muscular dystrophy, and by good absorption and distribution in tissues after administration to such mammals without acceleration of vascular permeability.

DETAILED DESCRIPTION OF THE INVENTION

In the present specification, unless otherwise noted, the term "alkyl" refers to both straight and branched chain alkyl groups, and the epoxysuccinic acid derivatives are the trans isomers, namely two carbonyl groups on the oxirane ring are in the trans configuration.

Preferred compounds of the present invention are the compounds of formula(I) wherein $R^1$ is hydrogen, $R^2$ is alkyl having 4 carbon atoms and n is an integer of 2 to 4.

A compound of formula(I) may be prepared, for example, in accordance with the following process: An epoxysuccinic acid monoester of the formula

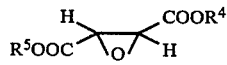
$$\underset{R^5OOC}{H}\!\!\diagdown\!\!\underset{O}{\diagup}\!\!\diagdown\!\!\underset{H}{\diagup}\!\!\overset{COOR^4}{} \quad (II)$$

wherein $R^4$ is hydrogen or alkali metal, and $R^5$ is $R^1$ other than hydrogen or alkali metal, may be treated with a chlorinating agent such as oxalyl chloride, thionyl chloride or the like to give the corresponding acid chloride. To the acid chloride, an amino acid compound of the formula

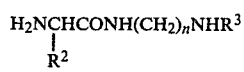
$$\underset{R^2}{\underset{|}{H_2NCHCONH(CH_2)_nNHR^3}} \quad (III)$$

wherein $R^2$, $R^3$ and n are defined above, may be added dropwise under ice cooling to give the compound of formula(I) wherein $R^1$ is $R^5$. In this amidation, the compound of formula(III) may be added with a base such as triethylamine, pyridine, methylmorphorine or the like. When the compound of formula(III) is employed directly in the form of an acid-addition salt, it may be provided for the reaction after removing the acid with a base such as an alkali hydroxide, triethylamine, pyridine or methylmorpholine; alternatively it may be allowed to react in the presence of the base mentioned above.

The compound of formula(II) wherein $R^4$ is hydrogen also can be directly converted to the compound of formula(I) wherein $R^1$ is $R^5$ without chlorinating. In this case, the compound of formula(II) wherein $R^4$ is hydrogen may be reacted with the compound of formula(III) in the presence of a condensing agent such as N,N'-dicyclohexylcarbodiimide, 1-ethyl-3(3-dimethylaminopropyl) carbodiimide or the like. Also preferred in this reaction is the addition of an N-hydroxy compound such as N-hydroxysuccinimide, 1-hydroxy-benzotriazole or the like.

Alternatively, the compound of formula (I) wherein $R^1$ is $R^5$ may be prepared by the amidation of the compound of the formula

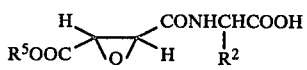
$$\underset{R^5OOC}{H}\!\!\diagdown\!\!\underset{O}{\diagup}\!\!\diagdown\!\!\underset{H}{\diagup}\!\!\overset{CONHCHCOOH}{\underset{R^2}{|}} \quad (IV)$$

wherein $R^2$ and $R^5$ are as defined above, with an amine of the formula

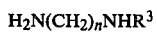
$$H_2N(CH_2)_nNHR^3 \quad (V)$$

wherein $R^3$ and n are as defined above. This amidation can be carried out by following the same procedure as that of the reaction of the compound of formula(II) wherein $R^4$ is hydrogen with the compound of formula(III).

As a further alternative, the compound of formula(I) wherein $R^1$ is $R^5$ may be prepared by ester-exchange reaction of the compound of formula(I), wherein $R^1$ is another group within the scope of $R^5$, with an alkcohol, which can form desired group of $R^5$, such as benzyl alcohol, cyclopentanol or cyclohexanol in the presence of a catalyst such as sulfuric acid, an alkali metal alcoholate or an alkali hydroxide such as sodium hydroxide, potassium hydroxide or the like.

The compound of formula(I) wherein $R^1$ is alkali metal may be prepared by a process which comprises treating the compound of formula(I) wherein $R^1$ is $R^5$ with an alkali hydroxide such as sodium hydroxide, potassium hydroxide or the like, and then, if necessary, following by addition of an organic solvent such as ethanol, acetone, ethyl ether, petroleum ether or the like.

The compound of formula(I) wherein $R^1$ is hydrogen may be prepared by a process which comprises acidifying the compound of formula(I) wherein $R^1$ is alkali metal with an inorganic acid such as hydrochloric acid or sulfuric acid, or an organic acid such as formic acid or acetic acid, and then, extracting with a suitable organic solvent such as ethyl acetate, ethyl ether, benzene or chloroform.

In the case where the compound of formula(I) has amino protected with benzyloxycarbonyl, such a protecting group may be removed by catalytic reduction using palladium-on-charcoal or palladium black.

The compounds of formulae(II) and (IV) can be prepared by the method as described in German Patent Laid Open Application No. P 28 09 036 or the like.

The compound of formula(III) can be prepared as follows: The compound of the formula

wherein $R^2$ is as defined above and $R^6$ is a protecting group, may be reacted with the compound of formula(V), followed by removal of the protecting group to give the desired compound. Examples of the protecting group are conventional groups in the field of peptide synthesis such as t-butoxycarbonyl, carbobenzoxy or methylbenzyloxycarbonyl. The amidation of the compound of formula(VI) with the compound of formula(V) can be carried out by following the same procedure as that of the reaction of the compound of formula(II) wherein $R^4$ is hydrogen with the compound of formula(III). Removal of the protecting group can be carried out according to the conventional manner in the field of peptide chemistry.

The following examples show representative compounds encompassed within the scope of the present invention and the manner in which such compounds are prepared. However, it is to be understood that the examples are for purposes of illustration only.

EXAMPLE 1

In 80 ml of the tetrahydrofuran were dissolved 1.00 g. of DL-trans-benzylhydrogenepoxysuccinate, 1.70 g. of N-L-leucyl-N'-benzyloxycarbonyl-1,7-diaminoheptane, 0.73 g. of 1-hydroxybenzotriazole and 0.55 g. of N-methylmorpholine. To the solution was slowly added 0.95 g. of 1-ethyl-3-(3-dimethylaminopropyl) carbodiimide hydrochloride under ice-cooling and stirring. The mixture was stirred for 2 hours under ice-cooling and then for 2 hours at room temperature. The solution was concentrated under reduced pressure and admixed with 100 ml of ethyl acetate and 100 ml of water and the mixture was shaken vigorously. The ethyl acetate layer was separated and washed successively with a 10% aqueous hydrochloric acid solution, an aqueous saturated bicarbonate solution and an aqueous saturated sodium chloride solution and concentrated to dryness. The resulting residue was purified by column chromatography on silica gel (chloroform:acetone=10:1) and recrystallized from ethyl acetate-n-hexane to give 1.50 g. of N-[N-(DL-3-trans-benzyloxycarbonyloxirane-2-carbonyl)-L-leucyl]-N'-benzyloxycarbonyl-1,7-diaminoheptane, m.p. 134° C. Yield: 67%.

EXAMPLE 2

Following the procedure of Example 1 and using 1.30 g. of DL-trans-benzylhydrogenepoxysuccinate and 1.75 g. of N-L-leucyl-N'-benzyloxycarbonyl-1,5-diaminopentane, there was obtained 1.80 g. of N-[N-(DL-3-trans-benzyloxycarbonyloxirane-2-carbonyl)-L-leucyl]-N'-benzyloxycarbonyl-1,5-diaminopentane, m.p. 145°-146° C. Yield: 66%.

EXAMPLE 3

Following the procedure of Example 1 and using 1.33 g. of DL-trans-benzylhydrogenepoxysuccinate and 1.84 g. of N-L-leucyl-N'-benzyloxycarbonyl-1,2-diaminoethane, there was obtained 1.87 g. of N-[N-(DL-3-trans-benzyloxycarbonyloxirane-2-carbonyl)-L-leucyl]-N'-benzyloxycarbonyl-1,2-diaminoethane, m.p. 148°-149° C. Yield: 61%.

EXAMPLE 4

Following the procedure of Example 1 and using 1.83 g. of DL-trans-benzylhydrogenepoxysuccinate and 1.38 g. of N-L-valyl-N'-benzyloxycarbonyl-1,4-diaminobutane, there was obtained 1.73 g. of N-[N-(DL-3-trans-benzyloxycarbonyloxirane-2-carbonyl)-L-valyl]-N'-benzyloxycarbonyl-1,4-diaminobutane, m.p. 179°-180° C. Yield: 58%.

EXAMPLE 5

Following the procedure of Example 1 and using 1.00 g. of DL-trans-benzylhydrogenepoxysuccinate and 1.54 g. of N-L-isoleucyl-N'-benzyloxycarbonyl-1,4-diaminobutane, there was obtained 1.65 g. of N-[N-(DL-3-benzyloxycarbonyloxirane-2-carbonyl)-L-isoleucyl]-N'-benzyloxycarbonyl-1,4-diaminobutane, m.p. 167°-168° C. Yield: 69%.

EXAMPLE 6

Following the procedure of Example 1 and using 1.15 g. of DL-trans-cyclohexylhydrogenepoxysuccinate and 1.68 g. of N-L-leucyl-N'-benzyloxycarbonyl-1,4-diaminobutane, there was obtained 1.71 g. of N-[N-(DL-3-trans-cyclohexyloxycarbonyloxirane-2-carbonyl)-L-leucyl]-N'-benzyloxycarbonyl-1,4-diaminobutane, m.p. 139°-141° C. Yield: 63%.

EXAMPLE 7

Following the procedure of Example 1 and using 1.07 g. of DL-trans-cyclopentylhydrogenepoxysuccinate and 1.68 g. of N-L-leucyl-N'-benzyloxycarbonyl-1,4-diaminobutane, there was obtained 1.56 g. of N-[N-(DL-3-trans-cyclopentyloxycarbonyloxirane-2-carbonyl)-L-leucyl]-N'-benzyloxycarbonyl-1,4-diaminobutane, m.p. 137°-139° C. Yield: 58.8%.

EXAMPLE 8

Following the procedure of Example 1, using 0.26 g. of DL-trans-benzylhydrogenepoxysuccinate and 0.21 g. of N-L-leucyl-N'-acetyl-1,4-diaminobutane, treating the product with column chromatography on silica gel (chloroform:methanol=50:1) and recrystallizing from chloroform-n-hexane, there was obtained 0.26 g. of N-[N-(DL-3-trans-benzyloxycarbonyloxirane-2-carbonyl)-L-leucyl]-N'-acetyl-1,4-diaminobutane, m.p. 181°-183° C. Yield: 59%.

EXAMPLE 9

Following the procedure of Example 8 and using 2.22 g. of DL-trans-benzylhydrogenepoxysuccinate and 2.20 g. of N-L-leucyl-N'-benzoyl-1,4-diaminobutane, there was obtained 2.60 g. of N-[N-(DL-3-trans-benzyloxycarbonyloxirane-2-carbonyl)-L-leucyl]-N'-benzoyl-1,4-diaminobutane, m.p. 146°-148° C. Yield: 64.7%.

EXAMPLE 10

In 100 ml of tetrahydrofuran were dissolved 2.90 g. of N-(DL-3-trans-benzyloxycarbonyloxirane-2-carbonyl)-L-leucine, 2.46 g. of N-benzyloxycarbonyl-1,4-diaminobutane carbonate, 1.92 g. of N-methylmorpholine and 1.30 g. of 1-hydroxybenzotriazole. To the solution was slowly added 1.8 g. of 1-ethyl-3-(3-dimethylaminopropyl)carbodiimide hydrochloride under ice-cooling and stirring. The mixture was stirred for 2 hours under ice-cooling and then for 2 hours at room temperature. The solution was concentrated under reduced pressure. The resulting residue was dissolved in a mixture of 150 ml of ethyl acetate and 150 ml of water. The solution was shaken vigorously and the ethyl acetate layer was separated. The ethyl acetate layer was washed successively with a 10% aqueous hydrochloric acid solution, a saturated aqueous bicarbonate solution and a saturated aqueous sodium chloride solution and concentrated to dryness. The resulting residue was crystallized from ethyl acetate-n-hexane to afford 3.00 g. of N-[N-(DL-3-trans-benzyloxycarbonyloxirane-2-carbonyl)-L-leucyl]-N'-benzyloxycarbonyl-1,4-diaminobutane, m.p. 169°–170° C. Yield: 65%.

EXAMPLE 11

In 20 ml of ethanol was dissolved 2.16 g. of N-[N-(DL-3-trans-benzyloxycarbonyloxirane-2-carbonyl)-L-leucyl]-N'-benzyloxycarbonyl-1,4-diaminobutane. To the solution was added dropwise 10 ml of an ethanol solution of 0.24 g. of potassium hydroxide with stirring. After stirring for 2 hours at room temperature, petroleum ether was added to the solution and the produced white precipitates of N-[N-(DL-3-trans-carboxyoxirane-2-carbonyl)-L-leucyl]-N'-benzyloxycarbonyl-1,4-diaminobutane potassium salt were collected on a filter. The precipitate was dissolved in 50 ml of water, made acidic with hydrochloric acid and extracted with ethyl acetate (50 ml×3). The ethyl acetate layers were combined, washed with saturated aqueous sodium chloride, dried on magnesium sulfate and concentrated to dryness. The resulting powders were recrystallized from chloroform-petroleum ether to obtain 1.30 g. of N-[N-(DL-3-trans-carboxyoxirane-2-carbonyl)-L-leucyl]-N'-benzyloxycarbonyl-1,4-diaminobutane, m.p. 56° C. Yield: 72%.

EXAMPLE 12

In 120 ml of methanol was suspended 2.00 g. of N-[N-(DL-3-trans-benzyloxycarbonyloxirane-2-carbonyl)-L-leucyl]-N'-benzyloxycarbonyl-1,4-diaminobutane and followed by addition of 0.20 g. of palladium black. The mixture was stirred vigorously in a weak stream of hydrogen at room temperature for 4 hours. The catalyst was filtered off and the filtrate was concentrated to about 20 ml. The residue was crystallized by addition of petroleum ether to give 1.10 g. of N-[N-(DL-3-trans-carboxyoxirane-2-carbonyl)-L-leucyl]-1,4-diaminobutane, m.p. 178°–181° C. (with decomposition). Yield: 95%.

The compounds of the present invention have superior inhibitory activity to CANP which exists in excess in muscle of mammals having muscular dystrophy, and superior absorption and distribution in tissues after administration to mammals as compared with the epoxysuccinic acid derivatives of German Patent Laid Open Application No. P 28 09 036 and Chemical Abstracts, 87, 68129a (1977). Their muscular dystrophy inhibitory activity was assayed by the method of Ishiura et al., [J. of Biochem., 84, 225 (1978)] using CANP prepared from a muscle of hereditary muscular dystrophy chicken, and the resulting value for 50% inhibition in the molar ratios for the enzyme expressed as $ID_{50}$ (mole/mole) is shown in Table 1 below.

The compounds of the present invention are better absorbed by the subcutaneous route in mammals such as rats or rabbits, as compared with the epoxysuccinic acid derivatives of the German Patent Laid Open Application described above and Chemical Abstracts, 87, 68129a (1977). To determine absorption, these compounds were administered subcutaneously to rats at a dose of 50 mg/kg, and the concentration of the test compound in rat plasma at an hour after the administration is shown in following Table 1.

TABLE 1

| Compound | CANP Inhibitory Activity $ID_{50}$ (mole/mole) | Concentration in rat plasma (μg/ml) |
|---|---|---|
| 2 | 121 | 1.5 |
| 4 | 113 | 1.2 |
| 5 | 92 | 1.4 |
| 6 | 75 | 1.5 |
| 8 | 100 | 1.8 |
| 9 | 89 | 1.3 |
| 10 | 78 | 1.6 |
| 11 | 19 | 13 |
| 12 | 55 | 25 |
| A | 5,400 | below 1.0 |
| B | 410 | below 1.0 |
| C | 580 | " |
| D | 574 | " |
| E | 4,600 | " |

Note
The number in the compound column of Table 1 refers to a compound which is prepared in accordance with correspondingly numbered foregoing Example. Also, Symbols A–E in the compound column of Table 1 refer to the following known compounds:
A: Ethyl hydrogen epoxysuccinate
B: Benzyl hydrogen epoxysuccinate
C: N—(3-ethoxy-carbonyloxirane-2-carbonyl)-L-leucine benzyl ester
D: N—(3-carboxyoxirane-2-carbonyl)-L-phenylalanine benzyl ester
E: N—(3-carboxyoxirane-2-carbonyl)-L-leucine The compounds of the present invention also inhibit effectively and specifically thiol proteases such as papain, bromelains and some kinds of cathepsin in which some sulfhydryl groups are essential for activity. On the other hand, they have neither inhibitory activity against proteolysis of casein by trypsin, chymotrypsin, pepsin, an acid protease of Paecilomyces varioti or Nagase (trademark of Nagase Industry), against esterolysis of benzoylarginine ethyl ester by kallikrein nor against fibrinolysis by human plasmin.

Papain inhibitory activity of the compounds of the present invention was assayed by the method of K. Hanada et al. [Agric. Biol. Chem., 42, (3) 523 (1978)] using papain (80 μg/ml, Sigma Chem. Co.) after twice crystallization. The amounts of inhibitor for 50% inhibition was expressed as $ID_{50}$ and shown in Table 2.

TABLE 2

| Compound | $ID_{50}$ (μg) | Compound | $ID_{50}$ (μg) |
|---|---|---|---|
| 1 | 0.302 | 7 | 0.164 |
| 2 | 0.481 | 8 | 0.123 |
| 3 | 0.203 | 9 | 0.181 |
| 4 | 0.436 | 10 | 0.260 |
| 5 | 0.323 | 11 | 0.118 |
| 6 | 0.142 | 12 | 0.106 |

Note
The numbers in the compound column of Table 2 are as defined with reference to Table 1.

The compounds of the present invention show no side-effects such as acceleration of vascular permeability and are superior to E-64 and its intermediates in this regard.

The pharmaceutical forms contemplated by the present invention include pharmaceutical compositions suited for oral, parenteral, and rectal use, e.g., tablets, powder packets, cachets, dragees, capsules, solutions, suspensions, sterile injectable forms, supporsitories, bougies, and the like. The carrier employed may be, for example, either a solid or liquid. Examples of solid carriers are lactose, terra alba, sucrose, talc, gelatin, agar, pectin, acacia, magnesium stearate, stearic acid and the like. Examples of liquid carriers are syrup, peanut oil, olive oil, water and the like. Similarly, the carrier or diluent can include any time delay material well known to the art, such as glyceryl monostearate or glyceryl distearate alone or with a wax.

The compounds of the present invention can be used to inhibit CANP which exists in excess in muscle of muscular dystrophy mammals, by the administration of about 5 to 400 mg/kg/day in single or two to four divided doses in oral or injectable preparations as described above.

The compounds of the present invention are of extremely low toxicity. That is, they show hardly any oral acute toxicity to mice at the dosages less than 2 g/kg of body weight. Moreover, no side-effects were observed after administration of 1 g/kg/day orally for 30 days to laboratory mice.

What is claimed is:

1. An epoxysuccinyl amino acid derivative of the formula

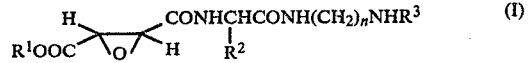

wherein $R^1$ is hydrogen, $R^2$ is a branched chain alkyl having 4 carbon atoms, $R^3$ is hydrogen or benzyloxycarbonyl, and n is an integer of 2 to 4.

2. A pharmaceutical composition having a thiol protease inhibitory effect comprising an effective amount of the compound of claim 1 and an inert carrier.

3. A method of inhibiting the activity of calcium-activated neutral thiol protease in a mammal having muscular dystrophy which comprises administering to said mammal an effective amount of the composition of claim 2.

* * * * *